United States Patent
Theisen

(10) Patent No.: US 7,022,331 B2
(45) Date of Patent: Apr. 4, 2006

(54) THERMOCHROMIC/PHOTOCHROMIC COSMETIC COMPOSITIONS

(75) Inventor: Lyle Theisen, 308 Third St. NE., Dyersville, IA (US) 52040-1224

(73) Assignee: Lyle Theisen, Dryersville, IA (US)

(*) Notice: Subject to any disclaimer, the term of this patent is extended or adjusted under 35 U.S.C. 154(b) by 380 days.

(21) Appl. No.: 09/843,219

(22) Filed: Apr. 26, 2001

(65) Prior Publication Data

US 2002/0192247 A1 Dec. 19, 2002

(51) Int. Cl.
*A61K 6/00* (2006.01)
*A61K 7/021* (2006.01)
*A61K 7/035* (2006.01)

(52) U.S. Cl. .................... 424/401; 424/63; 424/69; 514/71

(58) Field of Classification Search ............... 424/401, 424/63, 69, 70.6; 544/71
See application file for complete search history.

(56) References Cited

U.S. PATENT DOCUMENTS

| | | | |
|---|---|---|---|
| 4,421,560 A | 12/1983 | Kito et al. | |
| 4,560,604 A | 12/1985 | Shimizu et al. | |
| 5,017,225 A * | 5/1991 | Nakanishi et al. | 106/21 |
| 5,166,345 A * | 11/1992 | Akashi et al. | |
| 5,431,697 A * | 7/1995 | Kamata et al. | 8/483 |
| 5,503,583 A | 4/1996 | Hippely et al. | |
| 5,582,766 A | 12/1996 | Jeon | |
| 5,591,255 A * | 1/1997 | Small et al. | 106/21 |
| 5,628,934 A * | 5/1997 | Ohno et al. | 252/586 |
| 5,700,453 A * | 12/1997 | Sato | 424/64 |
| 5,873,892 A | 2/1999 | Cohen | |
| 5,997,849 A | 12/1999 | Small et al. | |
| 6,012,464 A | 1/2000 | Hollowell et al. | |
| 6,080,415 A * | 6/2000 | Simon | 424/401 |
| 6,120,821 A | 9/2000 | Goodin et al. | |
| 6,123,952 A | 9/2000 | Lagrange | |
| 6,139,779 A | 10/2000 | Small et al. | |
| 6,346,237 B1 * | 2/2002 | Lemann et al. | 424/61 |

OTHER PUBLICATIONS

Hawley, G. The Condensed Chemical Dictionary, 1971, 8th Ed., Van NOstrand Reinhold Company, p. 100, 210.*
Carey, F. Organic Chemistry, 1992, McGraw-Hill, Inc. P1080-2.*

* cited by examiner

*Primary Examiner*—Sreeni Padmanabhan
*Assistant Examiner*—Gina C. Yu

(57) ABSTRACT

Novel thermochromic and/or photochromic compositions are described. The thermochromic compositions include a thermoset resin, fatty substance, water, and dye, while photochromic compositions include a benzene derivative and a binder, such as silica gel. When mixed, the ingredients of the thermochromic and photochromic compositions form chromic cells with an outer shell comprised of either the thermoset resin (in the case of thermochromic compositions) or potassium nitrate (in the case of photochromic compositions). When the chromic compositions are exposed to either a heat or light stimulus, the chromic cells compress to causing the dye within the cells to no longer be visible, thereby creating a color-changing effect.

20 Claims, No Drawings

THERMOCHROMIC/PHOTOCHROMIC COSMETIC COMPOSITIONS

FIELD OF THE INVENTION

The present invention relates to a novel cosmetic composition for hair and skin that creates unique color effects due to changes in light and temperature.

BACKGROUND OF THE INVENTION

Throughout the centuries, it has been common practice for men and women to apply colored cosmetic compositions to their face, body, and hair to enhance their appearance. Make-up compositions, including eye shadow, mascara, blush, lipstick, nail polish, and hair dye typically consist of one or more pigments in a cosmetically-acceptable vehicle.

A primary goal of cosmetics is to provide a uniform application of color that creates a visually pleasing effect. Colors range from those that are intended to enhance natural skin or hair color, those used to cover up or hide an undesired existing color, and those that are purely frivolous and ornamental. These latter colors gained popularity during the "punk rock" era of the 1980's, and have recently regained popularity, due largely to their widespread use by Dennis Rodman, and other celebrities.

Photochromic compounds are compounds that change color upon exposure to light, then revert back to their original color once the light source is removed. In comparison, thermochromic compounds are compounds that change color upon exposure to different temperatures. Photochromic and thermochromic compounds (hereinafter "chromic compounds") have been proposed for use in many types of coloring compositions, including inks, paints, and cosmetics.

For instance, U.S. Pat. Nos. 6,139,779 and 4,421,560 describe thermochromic ink formulations. It has been found, however, that the compositions of these patents tend to rapidly lose their thermochromic properties.

U.S. Pat. No. 6,123,952 describes the use of a photochromic-coloring agent in a cosmetic composition. However, the composition of this patent is thermally irreversible, such that once the photochromic properties of the composition have been activated, the composition can no longer revert back to its original color.

There is therefore a need in the art for a chromic coloring agent for use in cosmetic formulations that is reversible, and maintains its thermochromic/photochromic capabilities for a longer period of time than conventional chromic agents.

It is therefore a primary object of the present invention to provide a thermochromic and/or photochromic cosmetic composition that is reversible, such that once the chromic properties of the composition have been activated, the composition can revert back to its original color.

It is a further object of the present invention to provide a thermochromic and/or photochromic cosmetic composition that maintains its thermochromic/photochromic properties for a relatively longer period of time than conventional chromic agents.

It is a further object of the present invention to provide a thermochromic and/or photochromic cosmetic composition that allows the user to create unique color changing effects and combinations.

It is yet a further object of the present invention to provide a thermochromic and/or photochromic cosmetic composition that is easily applied and removed.

It is still a further object of the present invention to provide a thermochromic and/or photochromic cosmetic composition that is simple and economical to manufacture.

It is a further object of the present invention to provide a thermochromic and/or photochromic cosmetic composition that is shelf stable for at least two years.

These and other objects of the present invention will become clear from the following detailed description of the invention.

SUMMARY OF THE INVENTION

The present invention relates to a reversible thermochromic and/or photochromic cosmetic composition for use in aqueous hair and skin product formulations. The invention involves the formation of thermochromic cells having a thermoset resin protective shell on the outside, and a mixture of water, fatty substance, and dye on the inside. Photochromic cells of this invention combine benzene derivative with a binder, and optionally a nitrate salt, such as potassium or sodium nitrate.

The chromic cells of this invention are non-toxic and may be included in conventional water-based cosmetic formulations, including hair mousses, gels, mascara, eye shadow, blush, lipstick, etc. The photochromic and thermochromic cells may be used individually, or in combination to create unique coloring effects. They offer the advantage over prior art chromic compositions of providing reversible color changing effects that are maintained for significantly longer periods of time.

DETAILED DESCRIPTION OF THE PREFERRED EMBODIMENT

The present invention describes novel thermochromic and/or photochromic cosmetically acceptable compositions. The invention is based upon the unexpected finding chromic cells may be synthesized and placed in a water-based composition to produce a coloring composition that reversibly changes color upon activation by temperature and/or light. The cosmetic compositions of this invention are non-toxic and maintain their chromic effects for a period of at least two years.

Thermochromic compositions act and react by changes in temperature, and are therefore considered to be thermotropic. In contrast, photochromic compositions act and react to changes in light, and are therefore considered to be phototropic. Chromic compositions can be manufactured to change at various temperature ranges and/or amounts of light based upon the concentration of chromic ingredient(s). Photochromic compositions react based on both the amount of light, ranging in wavelengths from 0 to 300 nanometers, and the type of light to which they are exposed, including natural light from the sun, and artificial light created from fluorescent or incandescent bulbs. Specifically, natural light provides a more dramatic and intense color change.

As noted above, chromic compositions have been used for the past several years for various purposes. However, these compositions are deficient since they quickly lose their chromic capabilities. The present inventor has determined that this premature loss of chromic function is due to the destruction of the chromatic cell by organic solvents, such as alcohols, ketones, amino resin, aromatics, and petroleum solvents. Through continuous use, these products lose their ability to change color.

The present inventor has now discovered that, when placed in an a aqueous composition having a pH in the neutral range, the chromic cells of this invention maintain their ability to change color for a substantially longer period of time than conventional chromic compositions. Further, the chromic compositions of this invention may be designed to be thermochromic, photochromic, or both.

The thermochromic cells of this invention contain a thermoset resin as a primary ingredient which forms the outer shell of the chromic cell. Thermoset resins form a more durable protective shell than other types of resins, and may be selected from the group consisting of one or more of melamine-formaldehyde (MF), urea formaldehyde (UF), and urethane resins. MF is the preferred thermoset resin for use in the compositions of this invention due to its high surface hardness, clarity, gloss, brilliant and precise colors, and light fastness. MF is also preferred due to its high level of resistance to solvents and household chemicals.

MF is a colorless, crystalline substance belonging to the family of heterocyclic organic compounds, which are used primarily as a starting material in the manufacture of synthetic resins. Melamine resins are approved for contact with foodstuffs, and do not affect the flavor of foods, even at high temperatures. MF is commonly used in the preparation of a variety of moldable products, including dinnerware, kitchen utensils, bathroom sinks, bathroom accessories, ashtrays, caps and closures for the cosmetics industry, precision medical components, electrical components, electrical wallplates and switches, buttons, etc. MF resins are available from many sources and manufacturers. Some commercially available sources of MF resins are Resimene® AQ7550 manufactured by Solutia®, Glazal® and Melresin®, manufactured by Altintel Melamin Sanayii A. S. The latter may also be purchased from Perstorp's Compounds Incorporated. The chromic cells of this invention may include from about 20–40% by weight MF, with about 25–35% by weight being preferred, and about 31% by weight MF being most preferred.

The next ingredient of the thermochromic cells of this invention is from about 15–45% by weight of fatty substance. From about 25–35% by weight cholesterol is preferred and about 28% is most preferred. As used herein, the term fatty substance includes, but is not limited to, the compound $C_{27}H_{15}OH$, one or any mixture of straight chain monobasic carboxylic acids and associated fatty acids from edible fats and oils, including animal and plant oils formed from fatty acid esters of polyols, in particular liquid triglycerides, for example sunflower oil, corn oil, soybean oil, marrow oil, grapeseed oil, sesame oil, hazelnut oil, apricot oil, almond oil, fish oils, glyceryl triaprocaprylate, or plant or animal oils of formula $R_1COOR_2$ in which $R_1$ represents a higher fatty acid residue containing from 7–19 carbon atoms and $R_2$ represents a branched hydrocarbo-based chain containing from 3 to 20 carbon atoms, for example purcellin oil, liquid paraffin, liquid petroleum jelly, perhydrosqualene, wheatgerm oil, beauty-leaf oil, sesame oil, macadamia oil, grapeseed oil, rapeseed oil, coconut oil, grondnut oil, palm oil, castor oil, jojoba oil, olive oil, or cereal germ oil, fatty acid esters, alcohols, acetaylclycerides, octanoates, decanoates, or ricinoleates of alcohols or of polyalcohols, fatty acid triglycerides, glycerides, fluoro oils, and perfluoro oils, as well as synthetic oils, such as Olestra™.

The composition according to the invention can also comprise other fatty substances, which can be selected by a person skilled in the art based on his or her general knowledge, so as to give the final composition the desired properties, for example in terms of consistency and/or texture. These additional fatty substances can be waxes, gums, and/or pasty fatty substances of animal, plant, mineral or synthetic origin, as well as mixtures thereof.

Some appropriate forms of cholesteryl that may be used in the thermochromic cells of this invention include, but are not limited to, cholesteryl acetate, cholesteryl benzoate, cholesteryl butoxyphenylcarbonate, cholesteryl butyrate, cholesteryl caprate (decanoate), cholesteryl caproate (hexanoate), cholesteryl caprylate (octanoate), cholesteryl chloride, cholesteryl p-chlorobenzoate, cholesteryl chloroformate, cholesteryl p-chlorophenylacetate, cholesteryl 3-chloropropionate, cholesteryl cinnamate, cholesteryl 2,4-dichlorobenzoate, cholesteryl 3,4-dichlorobenzoate, cholesteryl 3,5-dinitrobenzoate, cholesteryl ethylcarbonate, cholesteryl formate, cholesteryl isobutyrate, cholesteryl isostearylcarbonate, cholesteryl isotridecylcarbonate, cholesteryl laurate (dodecanoate), cholesteryl linoleate, cholesteryl linolenate, cholesteryl methylcarbonate, cholesteryl myristate (tetradecanoate), cholesteryl nitrate, cholesteryl p-nitrobenzoate, cholesteryl nonanoate, cholesteryl p-nonylphenylcarbonate, cholesteryl oleate, cholesteryl oleylcarbonate, cholesteryl palmitate (hexadecanoate), cholesteryl p-phenyl, cholesteryl benzoate, cholesteryl propionate, cholesteryl trichloroacetate, cholesteryl hemisuccinate, cholesteryl sulfate, cholesteryl undecanoate, cholesteryl p-nonyloxybenzoate, cholesteryl stearate, cholesteryl dicholesteryl, and cholesteryl dicholestrylsebacate supplied by CT Specialties.

The thermochromic cells of this invention also contain from about 15–30% by weight water, preferably about 20–25% by weight, and most preferably about 22% by weight. Any type of water is acceptable for use in the invention, including sterile, distilled, ionized, and/or tap water.

The last required ingredient in the thermochromic cells is a dye. The type of dye used in the composition is not critical, so long as it is cosmetically acceptable, and compatible with the other ingredients in the composition. Non-toxic, cosmetic dyes are well known in the art, and include titanium dioxide, zirconium dioxide, cerium dioxide, zinc oxide, iron oxide, chromium oxide, ferric blue, chromium hydrate, carbon black, aluminosilicate polysulfides, manganese pyrophosphate, halo acid dyes, azo dyes, anthraquinone dyes, and ultramarines (blue, green, pink, red, violet) etc. Preferred dyes are colors specified in CFSAN listing of document 82.1051, and include FD&C Blue No. 1, FD&C Green No. 3, FD&C Red No. 4, FD&C Yellow No. 5, FD&C Yellow No. 6, etc. The chromic cells may include from about 10–30% dye by weight, with about 15–25% by weight being preferred, and about 19% being most preferred.

Photochromic cells made in accordance with this invention include a benzene derivative as a primary ingredient. Appropriate benzene derivatives include, but are not limited to, m-[(p-aminophenyl)azo]benzenesulphonic acid, m-[(4-amino-3-methoxyphenyl)azo]benzenesulphonic acid, 1-naphthylamineazobenzene-4-sulphonic acid, 2'-aminoazobenzene-2-sulphonic acid, 2-phenylazo-p-cresol, 3'-aminoazobenzene-3-sulphonic acid, 4- (4-dimethylaminophenylazo) phenyl, arsonic acid, 4- (4-nitrophenylazo)-resorcinol, 4-(N,N-dimethylamino)azobenzene-4'-isothiocyanate, 4,4'-diaminoazobenzene 4,4'-diethoxyazobenzene, 4-N,N-dimethylaminoazobenzene-4'-isothiocyanate, 4-amino-2', 3-dimethylazobenzene hydrochloride, 4-amino-4'-dimethylaminoazobenzene, 4 aminoazobenzene, 4-aminoazobenzene-3, 4'-disulphonic acid, 4'-aminoazobenzene-4-sulphonic acid, 4'-aminoazobenzene-4-sulphonic acid (sodium salt), 4-aminoazobenzene-4'-sulphonic acid sodium salt, 4-dimethylamino-2-methylazobenzene, 4-dimethylamino-2'2-methoylazobenzene, 4-dimethylamino-3'-methylazobenzene, 4-dimethylamino-4'-methylazobenzene, 4-dimethylaminoazobenzene, 4-dimethylaminoazobenzene 4'-isothiocyante, 4-dimethylaminoazobenzene-4'-sulphonyl chloride, 4-hydroxyazobenzene, 4-hydroxyazobenzene-4'-sulfonic acid, 4'-hydroxyazobenzene-4-sulphonic acid, 4-methoxyazobenzene, 4-nitrophenyldiazoaminoazobenzene, 4-phenylazo-phenylisothiocyanate, azobenzene, azoxybenzene, chrysoidine, and bariumbis [5-chloro-4-ethyl-2-[(2-hydroxyl-naphthyl)-azo]benzenesulphonate. Azobenzene is the preferred benzene.

The benzene derivative should be used in the photochromic cells in a concentration of at least 10% by weight. The preferred concentration is between about 10–60% by weight. When used in a concentration of at least 30% by weight of the photochromic cell, several of the benzenes, including azobenzene, 4-methoxyazobenze, azoxybenzene, benzenesulphonate, and 4-hydroxyzobenzene, may be used to impart a red color to the photochromic cells upon exposure to light. Persons skilled in the art can readily ascertain other benzene derivatives besides those specifically noted that are suitable for this purpose. In concentrations of less than about 30%, these benzene derivatives do not give the cells a noticeably red color. Even when not included in the photochromic cells for purposes of color, a benzene derivative is included in the cell in a concentration of at least 10% by weight to "activate" other types of color-imparting chemicals as described below.

The second ingredient in the photochromic cells of this invention is a binder. The binder imparts cohesive qualities to the materials in the photochromic cells and helps keep the ingredients of the photochromic cells intact. Binders are well known in the art, and include, but are not limited to starch, gelatin, sugars such as sucrose, glucose, dextrose, molasses, lactose, acacia, sodium alginate, extract of Irish moss, panwar gum, ghatti gum, carboxymethylcellulose, methylcellulose, polyvinylpyrrolidone, polyethylene glycol, ethylcellulose, waxes, crosscarmellose sodium MF, polyethylene polyols, lauroyl lysine, trilaurin (monoacid triglyceride) microcrystalline cellulose and silica gel. The only requirements of the binder is that it be cosmetically acceptable, compatible with the other ingredients of the formulation, and capable of providing sufficient cohesiveness to the ingredients in the cell. Silica gel is the preferred binder. Silica gel is well known in the art and may be synthesized or is available from many commercial sources, including FMC Pharmaceutical, Green Canyon, Carl Anderson, Global Trade Alliance and GeeJay. The photochromic cells may include from about 5–50% by weight binder, with about 15–30% by weight being preferred and about is 23% being most preferred.

The photochromic compositions may further include a salt that, when exposed to light, is capable of imparting a yellow color to the photochromic cells upon activation by the benzene derivative. This "yellow salt" may be selected from one or more of the group consisting of potassium nitrate, calcium nitrate, calcium citrate, potassium citrate. Potassium nitrate is the preferred yellow salt. The yellow salt in this invention may be included in the cells in a concentration of from about 15–85% by weight, with about 25–75% by weight being preferred and about is 55% being most preferred.

The photochromic compositions may also optionally contain a salt that imparts a blue color to the photochromic cells upon exposure to a light source. This "blue salt" may be selected from one or more of the group consisting of silver nitrate, sodium citrate, aluminum nitrate and sodium nitrate. Sodium nitrate is the preferred blue salt. The composition may include from about 0–60% by weight blue salt, with about 5–30% by weight being preferred and about 12% being most preferred.

When initially placed in the photochromic cells of this invention, the yellow salts and/or blue salts are white/clear crystals. Upon exposure to light, however, the benzene derivative produces metasilicic acid to "activate" the nitrate salts, causing them to change color to blue, yellow, or both, depending on the type(s) of nitrate salts used in the photochromic cells.

Based on the above-described interactions between the benzene derivative, yellow salts, and blue salts, it can be readily appreciated that a plethora of different color combinations and effects can be obtained. For example, if a blue salt is included in the formulation with at least 30% by weight of a red-color producing benzene derivative, upon exposure to light, the combination of red from the benzene derivative and the blue from the blue salt will produce a purple effect. Likewise, if a yellow salt is included with at least 30% by weight benzene derivative, the combination of red from the benzene derivative and yellow salt will produce an orange effect. However, for example, if a blue salt is included with less than 30% benzene derivative, the benzene derivative will not impart a red color to the cells and, thus, the cells will appear blue. Similarly, if a blue salt and a yellow salt are included with less than 30% benzene derivative, the combination of blue and yellow salts will produce a green effect. Further, varying concentrations of the salts may be used to produce different shades and hues.

The photochromic cells may optionally include a thermoset resin to encapsulate the ingredients. The thermoset resin may be included in the same concentrations described above with respect to the thermochromic cells.

The ingredients of the thermochromic and photochromic cells may be simply combined in any order and mixed to form slurry, which is then preferably agitated to create a fine emulsion. If a thermoset resin is included in the formulation, the cells should be heated for a time period and at a temperature sufficient to cure the resins. The preferred curing time and temperature is for about 10–30 minutes at a temperature range of from about 150–350° F. (65.6–176.7° C.), with about 20 minutes at about 220° F. (104.4° C.) being most preferred.

The pH level of the chromic cells of this invention should be maintained in a neutral range of between about 6.8 to 7.2. Buffering compounds may be added to the cells and/or the compositions to which they are added in order to maintain a desired pH range of between about 6.5–7.5. Buffers are well known in the art, and may include acetic acid, adipic acid, aluminum ammonium sulfate, aluminum potassium sulfate, aluminum sodium sulfate, etc. Any buffering agent is appropriate to maintain the desired pH range so long as it is cosmetically acceptable and compatible with the remaining ingredients of the cells/compositions.

It is also preferred to use a light stabilizer in the chromic cells, most preferably in the form of a Hindered Amine Light Stabilizer (HALS) to prevent the deterioration and longevity of the chromic cells. HALS are well known in the art, and may be comprised of one or more of (2-(2-hydroxy-5-t-octyphenyl) benzotriazole) or (2-Hydroxy-4-(n-octoxy-benzo-phenone) or (2,2'-Dihydroxy-4-methoxybenzophenone.) Commercial sources of HALS are Cygard® UV24, UV5411, and UV1164, manufactured by Cytec® in conjunction with Sanduvor® 3058 and 3055 manufactured by Clariant®.

The light stabilizer becomes contained in the cells to absorb any free flowing free radicals. If included, the HALS should be included in a concentration of from about 3–4% by weight, or from about 0–50% by weight of the cosmetic composition, with about 1–25% by weight being preferred with 3.5% by weight being most preferred.

The final composition may be optionally filtered by conventional means to remove any foreign particles or substances, and are preferably stored at a temperature ranging from about 45–75° F. The compositions are preferably not frozen, however, if freezing does occur the compositions may be gradually thawed and will still work for their intended purpose.

The chromic cells and/or their resulting cosmetic compositions are preferably stored in a plastic airtight container. They should not be placed in metal containers due to possible chemical interaction of the metal with the ingredients. Also, if the container is opened and more than half the total volume of the container is used, it is recommended that a small amount of water be added to only the top of the air-exposed surface, to prevent caking and drying. The chromic cells/compositions of this invention have a shelf-life of no less than two years without any noticeable deterioration.

The resulting chromic cells may be added to any water-based, cosmetically-acceptable formulation. Since the chromatic cells are aqueous themselves in nature, they may be incorporated into such formulations quite easily. The chromic cells may be preferably incorporated into the desired vehicle using any type of mixing device, such as a Turbo-emulsifier and or a 400 Series In-line Mixer from Ross Technologies. The preparation of cosmetically-acceptable formulations is well known to persons skilled in the art. Such formulations include mousses, gels, solutions, suspensions, lotions, sprays, etc.

As used herein, the term "cosmetically-acceptable" refers to the fact that the preparation is compatible with the other ingredients of the formulation and is safe for external application. As used here, the term "water-based" refers to the fact that the formulations of this invention do not contain sufficient amounts of organic solvents to be detrimental to, break down, or destroy the chromic cells of the compositions of this invention.

The cosmetic formulations of this invention may generally incorporate auxiliaries such as preservatives, bactericides, perfumes, substances for preventing foaming, dyes, pigments which have a coloring action, thickeners, surface-active substances, emulsifiers, softening, humidifying and/or humectant substances. The formulations may further include a variety of substances, including suitable stabilizers, and wetting agents as well as colorings, moisturizers, preservatives, and fragrances. These minors are added in small amounts and are conventionally known in pharmaceutical formulation work to enhance elegance. Such minors should comprise less than 1% of the overall composition. Cosmetic formulations of this invention will generally include from about 10–30% by weight of the chromic cells of this invention, with about 15–22% by weight and about 19% being preferred.

As noted above, thermochromic cells may also be combined with photochromic cells in the manufacture of cosmetic compositions that have both thermochromic and photochromic capabilities. The thermochromic and photochromic cells may be combined in any ratio depending on the degree of thermochromic or photochromic properties that are desired in the final cosmetic formulation. The total concentration of thermochromic/photochromic cells in the final product should still fall within the range of about 10–30% by weight of the composition.

The chromic cells/cosmetic compositions of this invention are formulated to maintain and change color at particular temperature ranges and/or degrees of light. Once the thermochromic cells reach the requisite temperature, the outer membranes of the chromic cells begin to contract, forcing pressure on the dye contained in the cells. As the cells continue to contract and become progressively smaller, the dye within becomes more refracted, and progressively less visible, until the color of the dye is no longer detectable. Thus, the hair or skin area to which the compositions are applied returns to their original color. Once the temperature level changes again to "deactivate" the cells, the cells begin expanding, thereby allowing the color of the dye to once again become visible.

The use of photochromic and thermochromic pigments jointly in the same formula can produce a second, third, and sometimes multiple colors. For example, by combining thermochromic blue and photochromic yellow, four colors can be achieved in one formula. When such a formulation appearing blue is applied to a black substrate, which has a surface temperature of 80° F. (26.7° C.). If the formula is then exposed to sunlight, the photochromic yellow will become active, and in combination with the blue thermochromic thereby creating a green film. Once the heat of the sunlight raises the temperature of the film to 90° F. (32.2° C.) or greater, the thermochromic blue becomes active, thus removing, and the green film will turn to yellow. When the film is completely removed from the sunlight and only if the temperature of the film is still greater than 90° F. (32.2° C.), the film is now transparent. The transparency of the film will allow the substrates own black color to show through the film.

Further, several thermochromic and/or photochromic cells become active at different temperature ranges and/or different light intensities can be "stacked" together to create many unique coloring effects. For example, a formulation of "stacked" thermochromic pigments can be applied to a black substrate and is not exposed to light. The "stacked thermochromic formulation" that is purple in color is applied to the substrate that is 60° F. (15.5° C.). At 70° F. (21.1° C.), the purple film will change to red due to the absence of blue thermochromic pigment, which has become active. Upon reaching 80° F. (26.7° C.), red thermochromic pigment will become active to produce an orange color. At 90° F. (32.2° C.), red thermochromic pigment will become active, leaving only the yellow thermochromic pigment. At 100° F. (37.8° C.) the yellow thermochromic pigment becomes active. The transparency of the film will allow the substrates own black color to show through the film. Furthermore, if the same formulation was exposed to light, at 100° F. (37.8° C.) or greater, and a blue photochromic cell was resident in the film, the film would now change to blue. If exposed to light during the ladder of temperature, changes the color hues would be dramatically different.

Photochromic cells function in a much different manner from that of thermochromic cells, whether or not a thermoset resin is present in the photochromic formula. The benzene derivative or "activator" responds to light and the amount and/or type light. Light is absorbed into the very dense prismatic structure of the benzene derivative. The light stimulates the benzene derivative into producing metasilicic acid, which reacts with the white prismatic salt molecules, causing them to change color. The removal of light causes the benzene derivative to cease producing metasilicic acid, thereby causing the cell to fall dormant and revert to their original color.

The chromic compositions may also include a "fixed color" dye that is added to the formulation to which the chromic cells have been or will be added. Since the thermoset resin micro-encapsulates the cells, they are impervious to other inert compounds, including the additional dye. The fixed dye thereby either clings to or surrounds the cell, rather than being incorporated within the cells. If included in the cosmetic formulations of this invention, the fixed color dye(s) will generally constitute from about 0–50% by weight of the cosmetic composition, with about 5–25% by weight being preferred with 10% by weight being most preferred. Thus, even when the cells are in their activated state, i.e. have compressed to hide the dye within, the fixed color outside the chromic cells is still visible. The fixed color may therefore be used to create a multitude of color effects. Fixed pigments are well known in the art and may include titanium dioxide, zirconium dioxide, cerium dioxide, zinc oxide, iron oxide, chromium oxide, ferric blue, chromium hydrate, carbon black, aluminosilicate polysulphides, manganese pyrophosphate, metal powders (silver, aluminum, carbon black). Other appropriate fixed pigments include, but are not limited to, lakes (calcium, barium, aluminum, or zirconium salts, acidic dyes such as halo acid dyes, azo dyes, and anthraquinone dyes.

For instance, the chromic compositions may include a blue dye as a fixed color, and a yellow dye within the chromic cells. Thus, when the composition is in an inactive state, both the blue and yellow dyes will be visible, creating a green coloring effect on the hair/skin area to which the composition is applied. However, when the cells are activated due to a change in light and/or temperature, the yellow dye within the chromic cells will be compressed, rendering the yellow dye invisible. Hence, only the blue dye will then be visible, and the area to which the composition is applied will appear blue.

In general, the more thermoset resin that is included in the chromic compositions of this invention, the less heat that is required to activate the chromic cells. Table 1 is a chart showing various concentrations of MF in cosmetic compositions, and their temperature ranges for activation of the chromic cells:

TABLE 1

46% by weight MF: changes color at 32–35° F.
31% by weight MF: changes color at 80–84° F.
15% by weight MF: changes color at 132–138° F.

The photochromic compositions of this invention do not necessarily require a certain amount of light in order to become activated. However, the more light to which the compositions are exposed, or the higher the concentration of the benzene, the more intense the color of the composition at lower light levels.

The following examples are offers to illustrate but not limit the invention. Thus, they are presented with the understanding that various formulation modifications as well as method of delivery modifications may be made and still are within the spirit of the invention.

EXAMPLE 1

Preferred Manufacturing Procedure for Thermochromic Compositions

Water, cholesterol, dye, oil, and thermoset resin are combined and agitated under low sheer to create a very fine emulsification. Because of the properties of the compounds, the oil and dye end up on the inside of the capsule and the water ends up on the outside, with the resin making up the encapsulation itself. The resin used in the encapsulation is a thermoset resin and is very hard after the proper amount of curing time. The resulting product is a slurry. The slurry is then introduced into a cosmetic vehicle, such as a gel or mousse formula by use of an in-line mixer under low sheer/agitation so as not to damage the crystal. If desired, a fixed color may be added to the final batch. The composition is then preferably filtered using a cartridge or housing filter.

EXAMPLE 2

Preferred Manufacturing Procedure for Photochromic Compositions

Photochromic manufacturing by introducing combining both salt in the formula at exact percentages based on weight, at very low to medium sheer. The activator is then introduced to the batch based on percentage by weight of total formula and should allow for thorough incorporation. The final ingredient of a binder should be added at this time and allowing ample time for incorportion and mixture is essential for the finished product creating a slurry. It is now that a thermoset resin may be used to perform micro-encapuslate of a photochromic cell. The composition is then preferably filtered using a cartridge or housing filter.

EXAMPLE 3

| Preferred Thermochromic Composition | |
| --- | --- |
| Ingredient | Weight % (of composition) |
| Melamine-Formaldehyde | 31.0 |
| Cholesterol | 28.0 |
| Water | 22.0 |
| Dye | 19.0 |
| Total | 100.0 |

EXAMPLE 4

| Preferred Photochromic Composition | |
| --- | --- |
| Ingredient | Weight % (of composition) |
| Potassium Nitrate | 55.0 |
| Silica Gel | 23.0 |
| Sodium Nitrate | 12.0 |
| Azobenzene | 10.0 |
| Total | 100.0 |

EXAMPLE 5

| Preferred Photochromic/Thermochromic Hair Mousse Composition | |
|---|---|
| Ingredient | Weight (% of Composition) |
| Thermochromic cells | 50.0 |
| Photochromic cells | 50.0 |
| Total | 100.0 |

These cells are then added to hair mousse, gels and/or conditioners in a concentration of 19% by weight of total formula.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence, which is effective to meet the objectives there intended, unless the context specifically indicates to the contrary.

What is claimed is:

1. A reversible cosmetic composition comprising:
a water-based cosmetically acceptable carrier;
a photochromic composition dispersed within the carrier, the photochromic composition having a concentration of 10–30% by weight of the reversible cosmetic composition;
a fixed color dye dispersed within the carrier and located exterior to the dispersed photochromic composition, the fixed color dye having a concentration of 5–25% by weight of the reversible cosmetic composition;
a light stabilizer dispersed within the carrier, the light stabilizer having a concentration of 3–4% by weight of the reversible cosmetic composition;
a bactericide dispersed within the carrier; and
wherein the reversible cosmetic composition has a pH in the range of about 6.8 to 7.2.

2. The composition according to claim 1, wherein the photochromic composition comprises a benzene derivative and a binder.

3. The composition according to claim 1, wherein the reversible cosmetic composition is shelf-stable for a time period of at least two years.

4. A reversible cosmetic composition comprising:
a water-based cosmetically acceptable carrier;
a photochromic composition dispersed within the carrier; and
a fixed color dye dispersed within the carrier and located exterior to the dispersed photochromic composition.

5. The composition according to claim 4, wherein the photochromic composition have a concentration of 10–30% by weight of the reversible cosmetic composition, and the fixed color dye has a concentration of 5–25% by weight of the reversible cosmetic composition.

6. The composition according to claim 4, further including a light stabilizer dispersed within the carrier, light stabilizer having a concentration of 3–4% by weight the reversible cosmetic composition.

7. The composition according to claim 4, further including a bactericide dispersed within the carrier.

8. The composition according to claim 4, wherein the reversible cosmetic composition has a pH in the range of about 6.8 to 7.2.

9. The composition according to claim 4, wherein the photochromic composition comprises a benzene derivative and a binder.

10. The composition according to claim 4, wherein the reversible cosmetic composition is shelf-stable for a time period of at least two years.

11. A reversible cosmetic composition comprising:
a water-based cosmetically acceptable carrier;
a thermochromic composition dispersed within the carrier;
a photochromic composition dispersed within the carrier, the photochromic and thermochromic compositions having a combined concentration of 10–30% by weight of the reversible cosmetic composition;
a fixed color dye dispersed within the carrier and located exterior to the dispersed photochromic and thermochromic compositions, the fixed color dye having a concentration of 5–25% by weight of the reversible cosmetic composition;
light stabilizer dispersed within the carrier, the light stabilizer having a concentration of 3–4% by weight of the reversible cosmetic composition;
a bactericide dispersed within the carrier; and
wherein the reversible cosmetic composition has a pH in the range of about 6.8 to 7.2.

12. The composition according to claim 11, wherein the photochromic composition comprises a benzene derivative and a binder.

13. The composition according to claim 11, wherein the thermochromic composition comprises from about 20–40% by weight thermoset resin, from about 15–45% by weight cholesterol, from about 15–30% by weight water, and from about 10–30% by weight dye.

14. The composition according to claim 11, wherein the reversible cosmetic composition is shelf-stable for a time period of at least two years.

15. A reversible cosmetic composition comprising:
a water-based cosmetically acceptable carrier;
a thermochromic composition dispersed within the carrier;
a photochromic composition dispersed within the carrier; and
a fixed color dye dispersed within the carrier and located exterior to the dispersed photochromic and thermochromic compositions.

16. The composition according to claim 15, wherein the photochromic and thermochromic compositions have a combined concentration of 10–30% by weight of the reversible cosmetic composition, and the fixed color dye has a concentration of 5–25% by weight of the reversible cosmetic composition.

17. The composition according to claim 15, further including a light stabilizer dispersed within the carrier, the light stabilizer having a concentration of 3–4% by weight of the reversible cosmetic composition.

18. The composition according to claim 15, further including a bactericide dispersed within the carrier.

19. The composition according to claim 15, wherein the reversible cosmetic composition has a pH in the range of about 6.8 to 7.2.

20. The composition according to claim 15, wherein the photochromic composition comprises a benzene derivative and a binder.

* * * * *